United States Patent
Endara et al.

(10) Patent No.: US 9,848,912 B1
(45) Date of Patent: Dec. 26, 2017

(54) ADJUSTMENT ASSEMBLY FOR EXTERNAL FIXATOR ASSEMBLY

(71) Applicants: Matthew James Endara, Miami, FL (US); Christopher David Endara, Miami, FL (US)

(72) Inventors: Matthew James Endara, Miami, FL (US); Christopher David Endara, Miami, FL (US)

( * ) Notice: Subject to any disclaimer, the term of this patent is extended or adjusted under 35 U.S.C. 154(b) by 27 days.

(21) Appl. No.: 15/092,721

(22) Filed: Apr. 7, 2016

Related U.S. Application Data (60) Provisional application No. 62/144,043, filed on Apr. 7, 2015.

(51) Int. Cl.
*A61B 17/56* (2006.01)
*A61F 2/00* (2006.01)
*A61B 17/64* (2006.01)

(52) U.S. Cl.
CPC ........ *A61B 17/6466* (2013.01); *A61B 17/645* (2013.01); *A61B 17/6416* (2013.01)

(58) Field of Classification Search
CPC ............ A61B 17/6466; A61B 17/6416; A61B 17/645; A61B 17/60; A61B 17/64; A61B 90/50; A61B 90/57; A61B 90/14; A61B 2090/364; A61B 2090/3983; F16B 39/24; F16B 39/282; Y10T 24/44299; Y10T 24/44573
USPC ............. 606/54–59, 250–253, 277, 278, 324
See application file for complete search history.

(56) References Cited

U.S. PATENT DOCUMENTS

| | | | |
|---|---|---|---|
| 6,565,564 B2 | 5/2003 | Hoffman et al. | |
| 7,041,103 B2 | 5/2006 | Hoffmann-Clair et al. | |
| 7,048,735 B2 * | 5/2006 | Ferrante ............... | A61B 17/645 606/59 |
| 7,699,848 B2 | 4/2010 | Hoffman et al. | |
| 7,722,609 B2 | 5/2010 | Bordeaux | |
| 8,361,120 B2 | 1/2013 | Gabelberger et al. | |
| 8,403,928 B2 | 3/2013 | Bordeaux | |
| 8,734,446 B2 | 5/2014 | Miller | |
| 8,758,343 B2 * | 6/2014 | Maughan ........... | A61B 17/6466 606/54 |
| 9,539,029 B1 * | 1/2017 | Muniz ................. | A61B 17/6416 |
| 2010/0262143 A1 | 10/2010 | Bordeaux | |
| 2011/0066151 A1 * | 3/2011 | Murner .............. | A61B 17/6466 606/54 |

(Continued)

*Primary Examiner* — Pedro Philogene
(74) *Attorney, Agent, or Firm* — Malloy & Malloy, P.L.

(57) ABSTRACT

An assembly for use in an external fixator, structured to adjustably interconnect at least one or a plurality of bone fixation rods to a pin clamp comprising a base structurally adapted for movable, adjustable interconnection between the pin clamp and the one or more rod clamps. An elongate support shaft is movable with the base and movably connected thereto and at least one or alternatively a plurality of rod clamps are mounted on the support shaft. Each of the plurality of one or more rod clamps is structurally adapted to secure a different fixation rod to the support shaft. The one or more rod clamps are movably connected and adjustably positioned on the support shaft in adjacent relation to one another. The base, the support shaft and one or more rod clamps are movably interconnected relative to one another to define a substantially universal disposition of said plurality of rod clamps relative to the pin clamp.

22 Claims, 9 Drawing Sheets

(56) References Cited

U.S. PATENT DOCUMENTS

2012/0089142 A1\* 4/2012 Mullaney .......... A61B 17/6466
606/54
2013/0165931 A1 6/2013 Bordeaux \* cited by examiner

ADJUSTMENT ASSEMBLY FOR EXTERNAL FIXATOR ASSEMBLY

CLAIM OF PRIORITY

The present application is based on and a claim of priority is made under 35 U.S.C. Section 119(e) to a provisional patent application that is in the U.S. Patent and Trademark Office, namely, that having Ser. No. 62/144,043 and a filing date of Apr. 7, 2015, and which is incorporated herein by reference.

BACKGROUND OF THE INVENTION

Field of the Invention

The present invention is directed to an assembly for use in combination with in an external fixator and is structured to adjustably interconnect one or more bone fixation rods to a pin clamp in a manner which significantly enhances the ability to dispose the one or more fixation rods relative to the pin clamp and bone pins operatively associated therewith, in a preferred orientation to efficiently, reliably and correctly stabilize the skeletal component, with which the external fixator is procedurally associated.

Description of the Related Art

Many bone fractures are complex and cumbersome to treat. Accordingly, not all bone fractures heal within the same time. Simple fractures take far less time to heal, if no other complications are involved. On the other hand, most complex bone fractures can take several weeks to heal. In any event, a broken bone has to be stabilized and supported until it is strong enough to handle external factors like body weight and movement.

Assuming the above, medical practitioners can typically treat a bone fracture with internal fixation assemblies and/or external fixation assemblies depending on the nature and severity of the fracture. In internal fixation, the surgeon typically conducts a surgical procedure to set the bone fracture in place. As such, the bone fragments may be first repositioned into the normal alignment and secured with special implants such as plates, screws and wires.

In contrast, external fixation assemblies or "external fixators" involves a surgical treatment used to stabilize broken bones at a predetermined proximity from the operative or injury area. In external fixation, metal bone pins typically including a threaded structure are attached to the bone after passing through miniscule incisions into the skin and muscle portions associated with the site of the broken bone. The bone pins are secured to a pin clamp or like pin securing device located exteriorly of the corresponding body part, outside the skin. In addition, in order to provide adequate stability and elongated bone fixation rod serve to interconnect the pin clamps and corresponding ones of the bone pins which are secured to different bone segments on opposite sides of the break or fracture. Accordingly, external fixators provide unhindered contact to the relevant skeletal structures for their initial assessment. External fixators also allow for secondary interventions which may be desirable to restore bony continuity of skeletal structures of the body.

Accordingly, it is recognized that external fixator assemblies do in fact exist and are used in the medical profession for an appropriate procedure relating to the healing, mending, and stabilizing, of broken or fractured bones. However, many of the known external fixator devices or and/or assemblies have at least somewhat limited operability at least to the extent of adjusting the operative components thereof so that the bone pins, pin clamp, and bone fixation rods can be properly positioned and oriented relative to one another to facilitate a stabilization and healing of the skeletal component being treated.

More specifically, many known or conventional external fixator assemblies do not have sufficient versatility, at least in terms of facilitating adjustable orientation of the external fixator assembly, to allow precise and accurate positioning thereof in the bone stabilization process. Accordingly, an imprecise positioning and/or orientation of external fixators as well as the lack of adequate stabilization can restrict the joint motion, cause infections and take much longer for the broken bone to heal.

Therefore, there is a need in the medical profession for an assembly structured for operative association with an external bone fixator that facilitates the precise positioning and orientation of the various components of the external fixator assembly including, but not limited to, relative placement of the pins, pin clamp and bone fixation rod. Further, in many of the more complex bone breaks or fractures it is necessary and/or desirable to interconnect associated bone pins and corresponding pin clamps used to treat a common break or fracture with a plurality of the aforementioned bone fixation rods in order to increase, maintain or assure proper stability.

More specifically, such a preferred adjustment assembly should be capable of a substantially universal range of motion and positioning of one or more bone fixation rods relative to an associated and/or corresponding pin clamp and bone pins. Further, such an adjustment assembly should have sufficient versatility to be used with a single pin clamp or a plurality of pin clamps while maintaining the ability to substantially universally position operative components of the external fixator as believed necessary by medical personnel.

SUMMARY OF THE INVENTION

This invention is intended to present a solution to these and other needs which remain in the relevant field of art. As such, these and other objects, features and advantages of the present invention will become clearer when the drawings as well as the detailed description are taken into consideration.

More specifically, the present invention is directed to an adjusting assembly for use in combination with an external fixator device. The assembly is structured to adjustably interconnect and substantially universally position one or more fixation rods in stabilizing relation to a pin clamp and associated bone pins embedded in the skeletal component being treated. Moreover, the structural features of the one or more embodiments of the adjusting assembly of the present invention significantly enhances the versatility of conventional and/or customized external fixators, at least to the extent of facilitating a preferred positioning of the pin clamp and associated bone pins relative to one or more stabilizing bone fixation rods.

Accordingly, at least one preferred embodiment of the adjustment assembly comprises a base including an elongated shank portion and a head portion fixedly secured thereto. The shank of the base is dimensioned and configured to be telescopically inserted or otherwise movably attached to a conventional or customized coupling structure. In turn, the coupling structure serves to interconnect the pin clamp to a remainder of the external fixator and directly to the adjustment assembly of the present invention. Therefore, when in an assembled mode, the shank and the head of the base are movably and more specifically rotationally connected to the pin clamp coupling member. As set forth in greater detail hereinafter, additional structural features are associated with and/or integrated in the base in order to facilitate the enhanced, substantially universal positioning of at least one and, when preferred, a plurality of fixation rod clamps.

In addition, an elongated support shaft is movably connected to the base and extends radially and linearly outward from the head portion while being connected thereto. Further, the cooperative structural features of the base and the support shaft facilitate the positioning of the support shaft outwardly from the head portion at least in a substantially radial direction. As such, a connecting structure, preferably in the form of a ball and socket connecting structure is integrated in a corresponding end portion of the support shaft as well as a receiving portion of the base. The ball and socket connection is disposed and structured to facilitate a rotational/pivotal attachment of the support shaft relative to the head portion and shank. As such, the support shaft is movable with the base and is also pivotal outwardly there from through a predetermined and preferred arcuate path. In at least one preferred embodiment the arcuate path of the support shaft may extend along substantially 180°.

To facilitate a substantially universal range of motion and placement of the one or more fixation rod clamps, the head portion of the base includes at least one elongated channel formed therein and preferably extending across the entirety of the head portion. Further, the channel may include oppositely disposed open ends. As such, the support shaft may be disposed radially outward from the head portion when in a substantially perpendicular relation to the shank or length of the base. In such a radial orientation, the support shaft is disposed along a length of the channel, while extending outwardly from one of the open ends thereof. Therefore, the support shaft may move with the base while being disposed in the aforementioned radial orientation concurrently to being substantially perpendicular to the length of the base or shank.

However, the overall length of the support shaft is such that a significant portion thereof extends beyond the head and/or channel in which it may be operatively disposed. As a result, the length of the support shaft is sufficient to have movably and adjustably mounted thereon at least one but in certain preferred instances a plurality of at least two fixation rod clamps. Moreover, each of the rod clamps is disposed and structured to engage and or "clamp" a different one of a corresponding number or plurality of bone fixation rods. As a result, additional stability may be provided to an exterior fixator assembly when required to maintain cooperatively disposed pin clamps and pins in a stable relation to one another and to the skeletal component being treated.

In addition, an adjustment assembly is movably and adjustably connected to the support shaft in cooperative relation to the one or more rod clamps. As a result, predetermined manipulation of the adjustment assembly will serve to increase or otherwise facilitate the clamping and/or gripping force each of the one or more rod clamps will exert on a corresponding bone fixation rod with which it is engaged.

Therefore and as described in greater detail hereinafter, the structural and operative features of the adjustment assembly of the present invention is capable of defining a substantially universal range of motion and or disposition of the one or more rod clamps operatively connected to the support shaft thereby facilitating a preferred and accurate orientation of one or more bone fixation rods relative to one or more interconnected pin clamps and associated bone pins embedded in the bone of the patient.

As used herein, the term "universal" is more definitively defined as a combination of relative movements of the base, the support shaft and the plurality of rod clamps being movably interconnected to one another to define a substantially "universal" disposition of the one or more rod clamps and associated fixation rods relative to the one or more pin clamps, which is intended to be stabilized.

In even more specific terms, the base is preferably rotational relative to the pin clamp coupling member; the support shaft is pivotally/rotationally connected to and movable with the base, as the base moves relative to the coupling member and the one or more rod clamps are adjustably movable and positionable on the support shaft and movable therewith, as the support shaft moves with and relative to the base and the base moves relative to the coupling member and corresponding pin clamp. As a result, the one or more rod clamps may be effectively oriented and positioned throughout a substantially universal range of movement and disposition. This results in facilitating an enhanced and preferred orientation of the one or more bone fixation rods relative to the pin clamp and bone pins anchored into the skeletal component of the patient.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As represented throughout the accompanying Figures and with initial and primary reference to FIGS. 1-4, the present invention is directed to an adjustment assembly generally indicated as 10, intended to be used in combination with an external fixation assembly.

Figure 9:
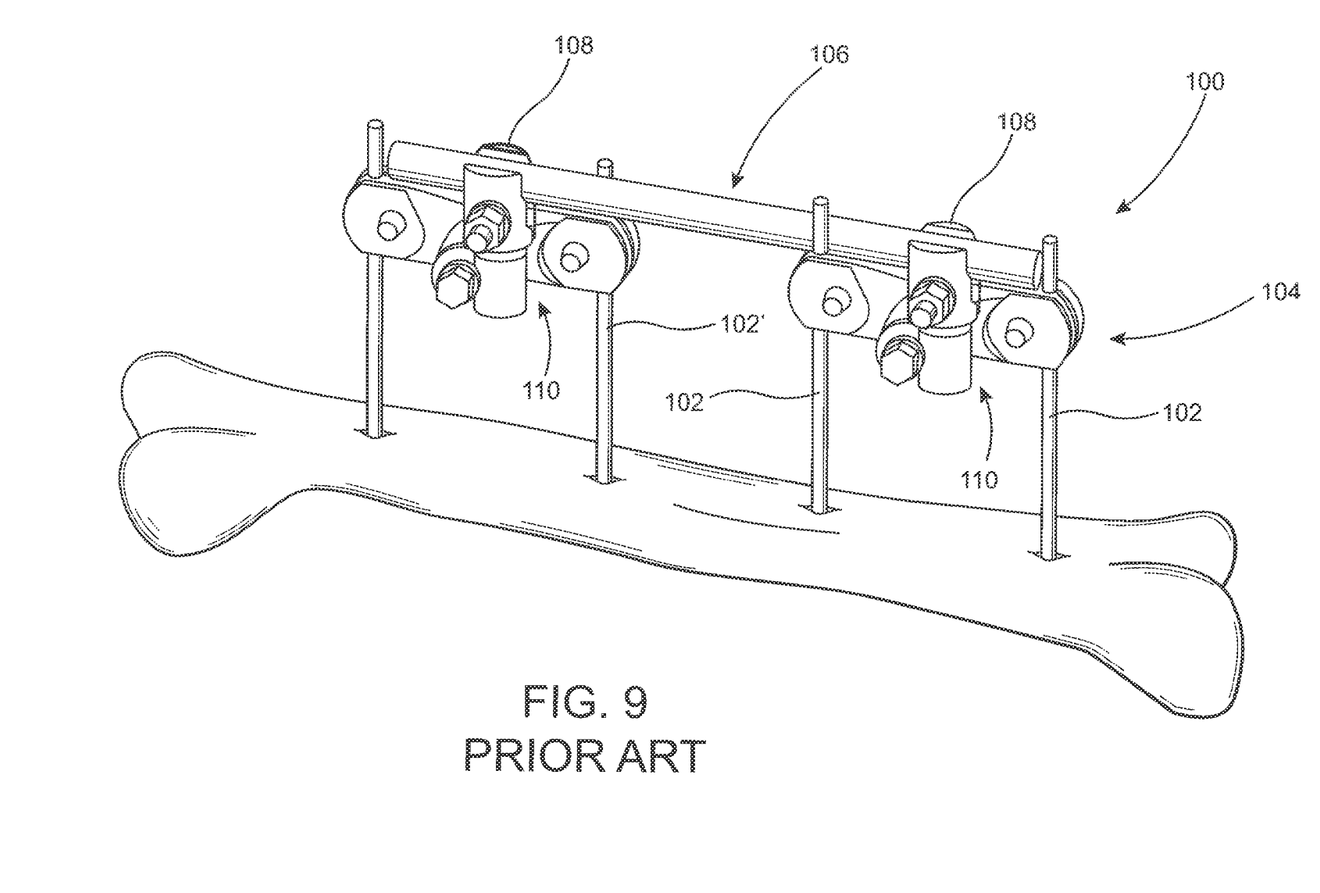
FIG. 9 is a perspective view of a prior art external fixation assembly operatively associated with a skeletal component being treated.

In order to clarify the environment in which the assembly 10 is utilized, FIG. 9 discloses a known and/or prior art example of an exterior fixator assembly generally indicated as 100. As practically applied, a plurality of bone pins 102 are embedded in a bone or skeletal component under treatment. In addition, while not shown in the example represented in FIG. 9, one or more pin clamps or like gripping devices 104 are positioned on the exterior of the user's body adjacent the bone under treatment. As such, the plurality of bone pins pass through soft-tissue components of the area into embedded relation with the bone, as represented. A stable, relative disposition between the pin clamps 104 is accomplished by their interconnection using a leg fixation rod 106. The interconnecting relation of the fixation rod 106 provides stability to the overall exterior fixation assembly 100. In addition, the plurality of pin clamps 104 are connected to the bone pins 102 so as to maintain them in an intended position relative to one another and to other, cooperatively positioned bone pins 102' also embedded in the bone being treated. The pin clamps 104 are stabilized through the provision of the one bone fixation rod 106 disposed in interconnecting relation to and between the pin clamps 104. Fixation rod clamps 108 are disposed in gripping, clamping relation to corresponding portions of the bone fixation rod 106 and serve to interconnect the fixation rod 106 to each of the pin clamps 104.

Further, a coupling member 110 is provided to interconnect each of the rod clamps 108 to a remainder of the corresponding pin clamps 104. As such, a movable relation between each of the rod clamps 108 is accomplished by the aforementioned coupling member 110. As is recognized in the medical profession proper placement of the bone fixation rod 106 relative to the interconnected pin clamps 104 is important in order to provide meaningful stability to the overall external fixator assembly 100.

The prior art structure represented in FIG. 9 is representative only of possibly structured external fixators but considered to be operable for its intended purpose and function. However, one factor not represented is the frequent requirement for the utilization of a plurality of bone fixation rods, as at 106, in order to provide additional stability in cases of severely damaged bone(s) or more difficult or complex damage to the bone(s) being fixated. Further, the proper orientation of the rod clamps 108 and bone fixation rod 106 is important in order to provide meaningful stability to the bone pins 102 regardless of their relative position and orientation.

Figure 7:
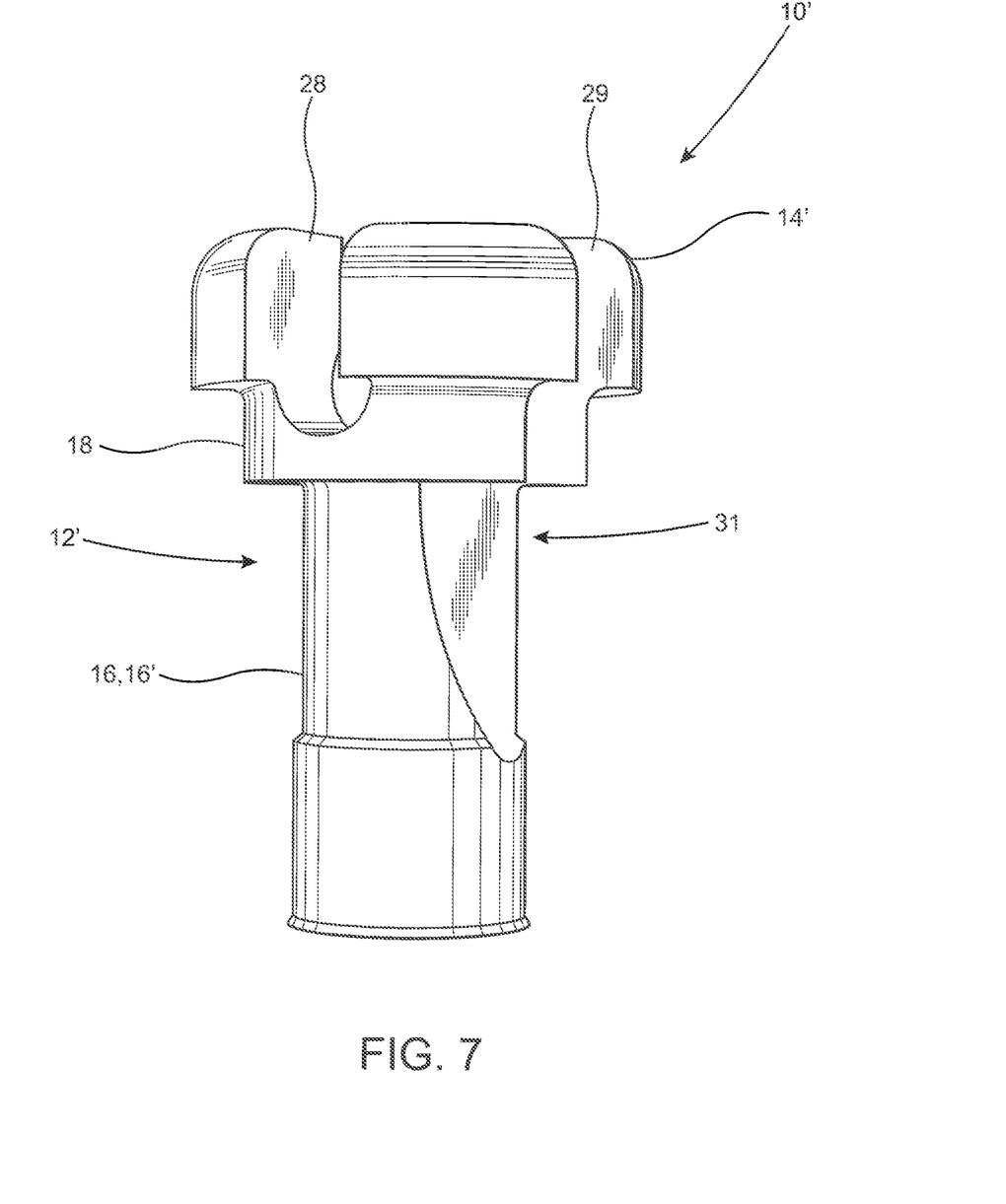
FIG. 7 is a perspective view of a base associated with the embodiment of FIGS. 5-7 and with structural modifications, associated with the embodiment of FIGS. 1-4.

Again, with primary reference to FIGS. 1-4, the adjustment assembly 10 of the present invention comprises a base generally indicated as 12 and 12' including a head portion 14, 14' and elongated shank or body portion 16 structurally modified in accord with one other embodiment of the present invention and represented in detail in FIG. 7. The shank 16 has a smaller transverse dimension than the somewhat enlarged head 14, 14' and is cooperatively dimensioned to pass telescopically within the interior of the housing 110' of the coupling member 110. In addition, one end of the shank 14 may be peened or otherwise structured to maintain the shank 14 within the interior of the housing 110'. In addition the base 12 includes a flange 18 or under portion of the head 14, 14' which is disposed in abutting relation to the open end 110" of the housing 110'. As a result, the shank 16 is effectively retained within the interior of the housing 110'. However, the shank 16 is further dimensioned and configured to allow rotation thereof within the housing 110' to further facilitate adjustable positioning of the remainder of the assembly 10 and allow a universal positioning of portions thereof. Such universal positioning facilitates more freedom of medical personnel to properly dispose, orient and align one or more bone fixation rods 106, as described in greater detail hereinafter.

Yet additional structural features associated with the base 12 are represented in the structurally modified base 12' represented in FIG. 7. More specifically an access opening 31 is integrally formed in at least a portion of the shank 16 and extends along a length thereof as represented. Further, the access opening 31 has an upper or innermost end disposed in communicating relation with channel 28. In addition, the ball 24 of the ball and socket connection 22 is allowed to be inserted into and removed from its rotational/pivotal attachment to the base 12 by passing through the upper end of the access opening 31 and along at least a portion of the length thereof. Assembly of the support shaft 20 into its universal movement relative to the base 12 is thereby facilitated.

The assembly 10 further includes an elongated support shaft 20 having one end movably connected and retained to the base 12 preferably by the aforementioned ball and socket connection 22. More specifically, one end of the support shaft 20 includes a ball structure 24 integrally or fixedly formed thereon. The ball structure 24 is received within a socket 25 integrated into an inner portion of the head 14, as represented in at least FIG. 4. Therefore, the ball and socket connection 22 between the support shaft 20 and the base 12 allows both a rotational and pivotal motion of the support shaft relative to the base 14 concurrently to facilitating movement of the support shaft with the base 14, as the shank 16 rotates within the interior of the housing 110'.

In order to accomplish what may be accurately referred to as a "universal" adjustable positioning of the assembly 10, relative to the coupling 110 and a pin clamp associated therewith, the head 14 further includes at least one elongated channel 28 formed therein. The channel 28 includes oppositely disposed open ends 28' through which the support shaft 20 may pass when disposed in a radially outward extended relation to the base 12, as represented throughout FIGS. 1-4. Such a radially outward extending relation is concurrent to the support shaft 20 being disposed in substantially perpendicular relation to a remainder of the base 12 specifically including the somewhat elongated shank 16. Moreover, it should be further noted that the provision of the ball and socket connection 22 facilitates a pivotal motion of the support shaft relative to the base 12 and head 14 through a substantially arcuate path as schematically represented by directional arrow 200 in FIG. 2. In at least one embodiment, the arcuate path includes a range of substantially 180°. In traversing the 180° arcuate path 200, the support shaft 20 will extend along the length of approximately one half of the channel 28 and extend through a corresponding open end 28' thereof. However, upon traversing the arcuate path 200 the support shaft will extend along the other half of the channel 28 and extend outwardly from the opposite open end 28'.

Figure 1:
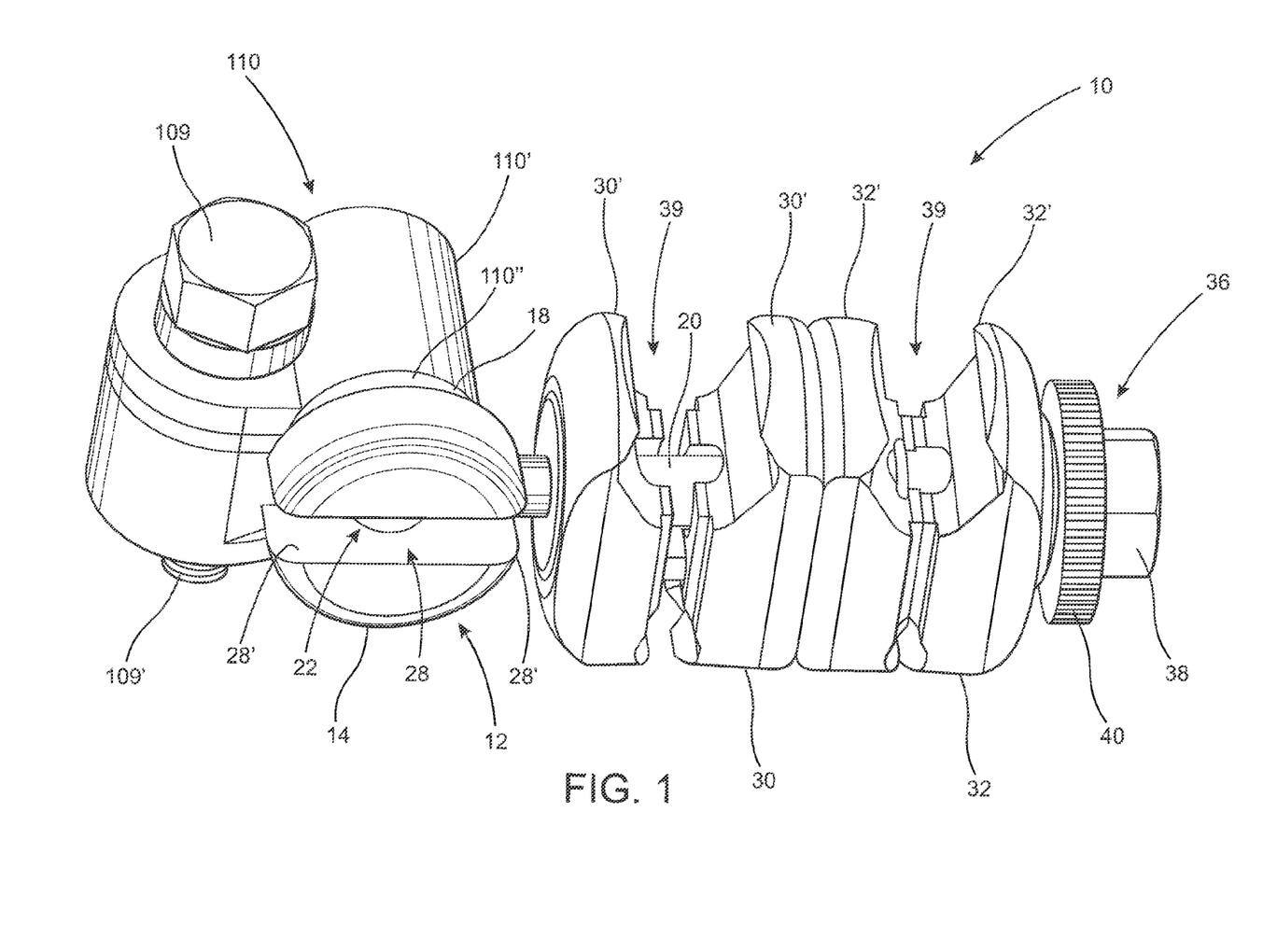
FIG. 1 is a perspective view of one preferred embodiment of the adjustment assembly of the present invention represented in an at least partially assembled relation to other components of an external fixator.
Figure 2:
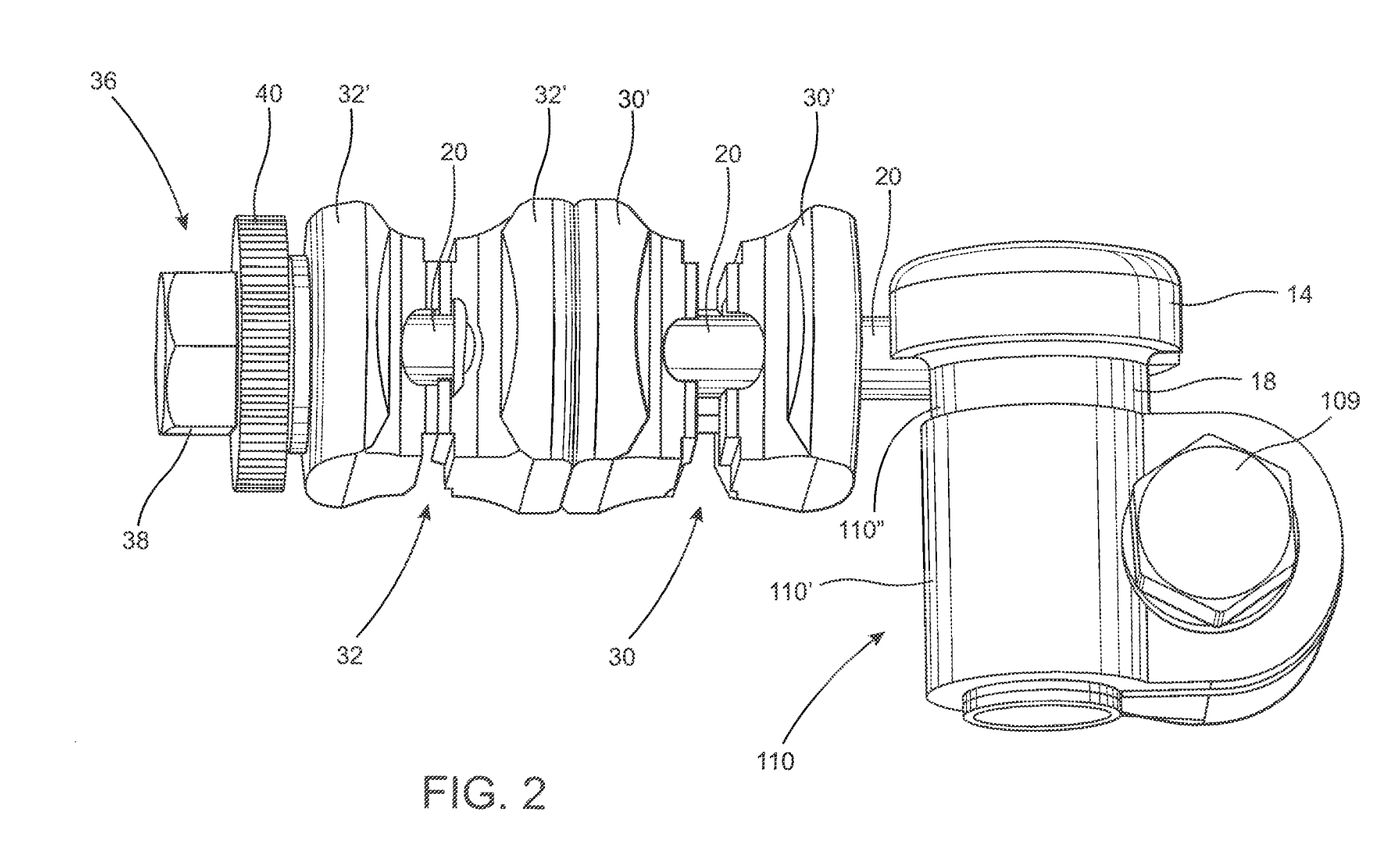
FIG. 2 is a top perspective view of the embodiment of FIG. 1.
Figure 3:
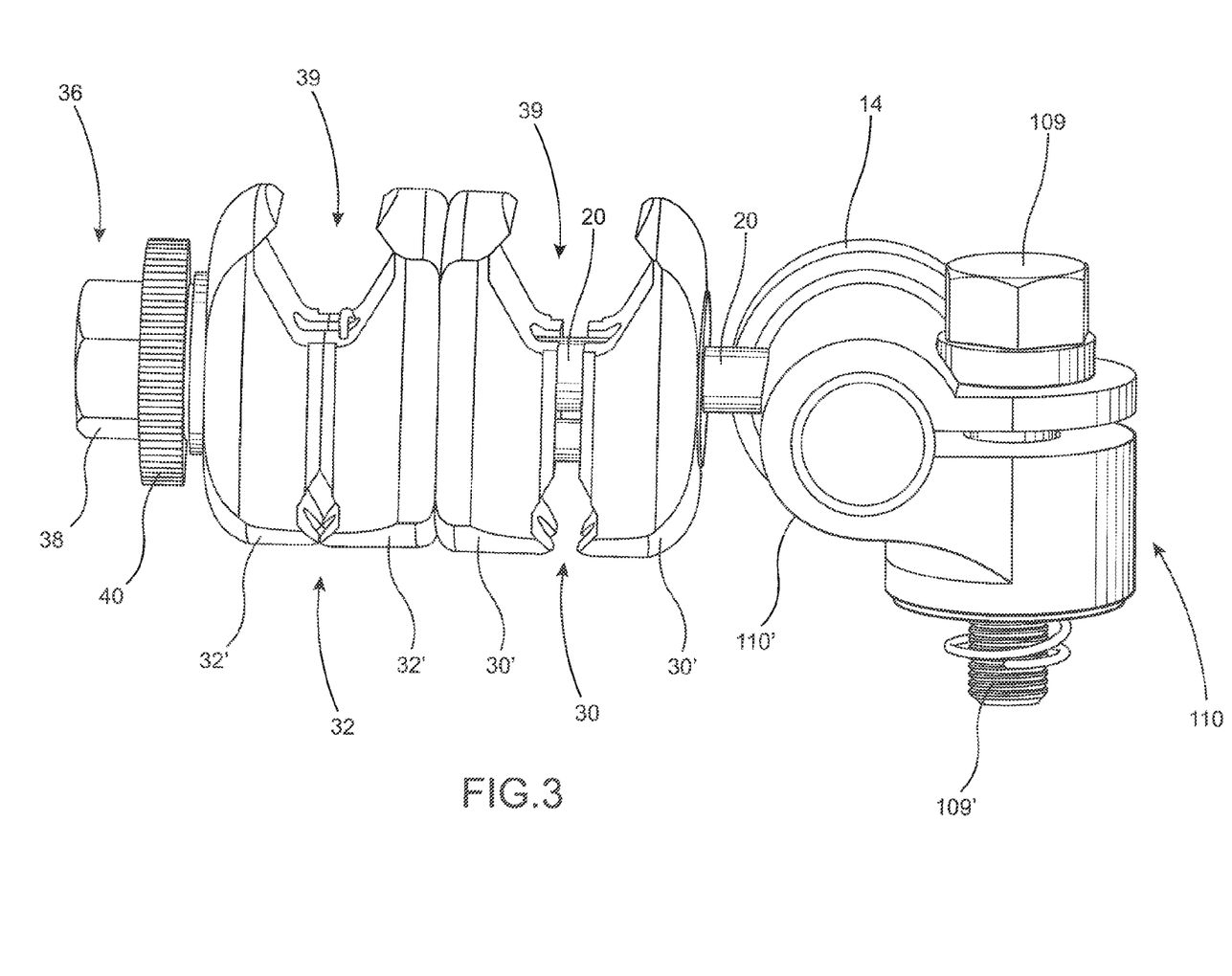
FIG. 3 is a side perspective view of the embodiment of FIGS. 1-2.
Figure 4:
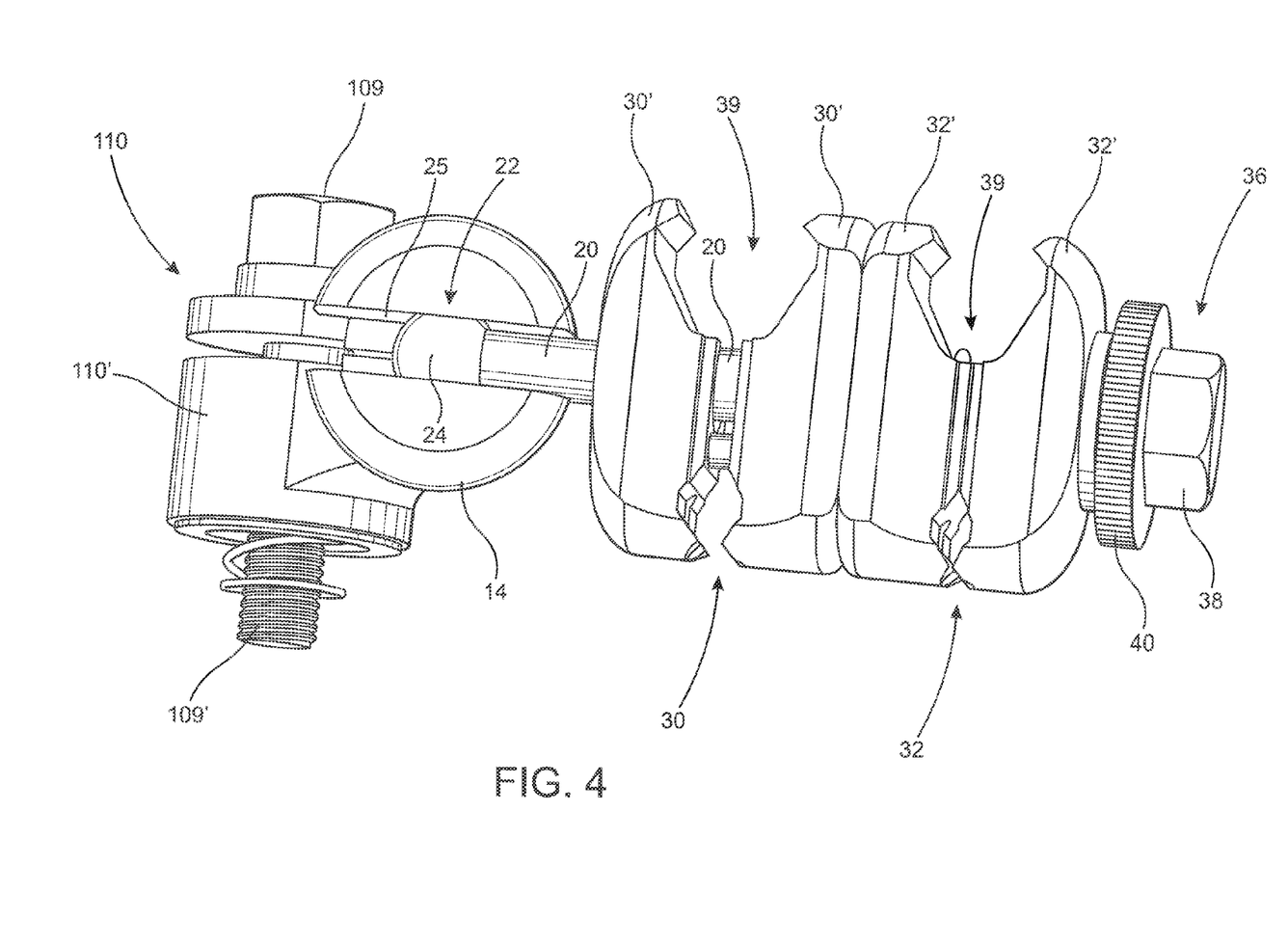
FIG. 4 is a side perspective view, opposite to that of FIG. 3, of the embodiment of FIGS. 1-3.
Figure 5:
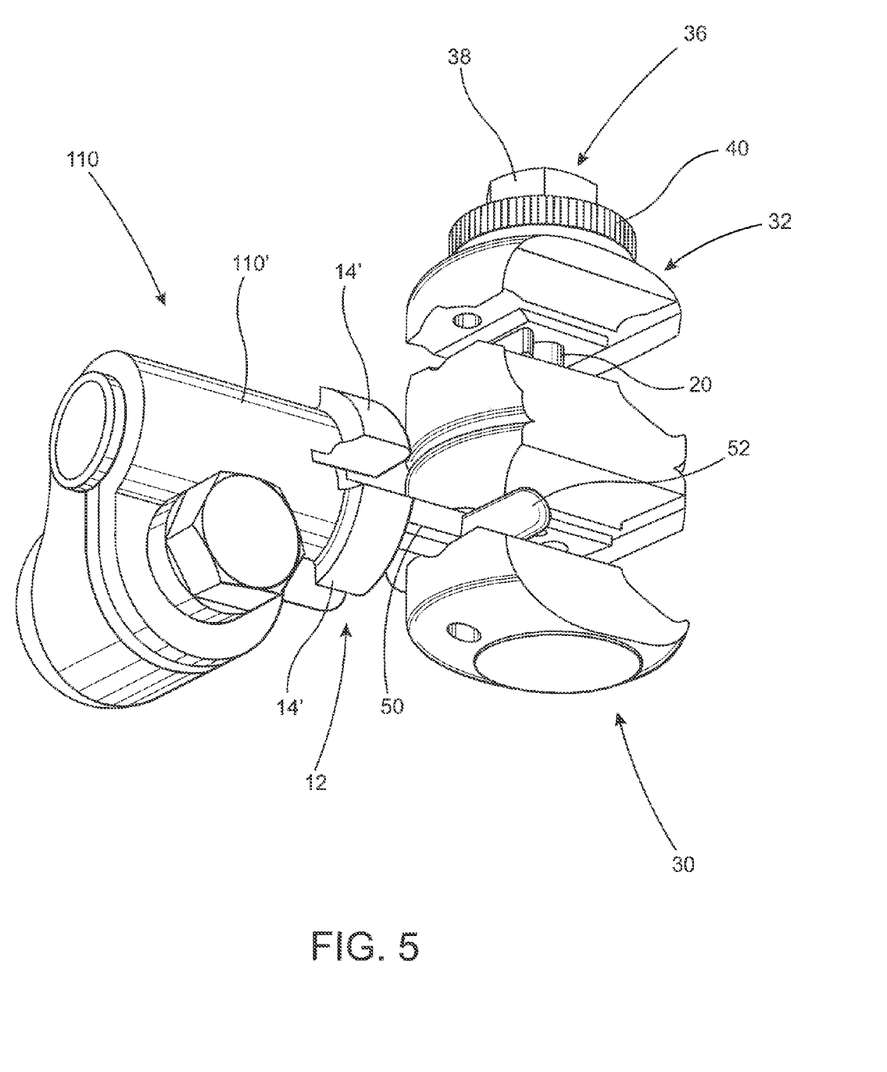
FIG. 5 is a perspective view of yet another preferred embodiment of the adjustment assembly of the present invention.

Therefore, in order to accomplish proper disposition and orientation of the assembly 10, the support shaft 20 may be pivoted about the ball and socket connection 22 and be disposed within the interior of the channel 28 so as to extend outwardly from either opposite end 28'. In addition, the adjustable versatility of the assembly 10 may be further demonstrated by a positioning of the support shaft linearly or angularly outward from the head 14 as perhaps more clearly demonstrated in the additional preferred embodiment of FIGS. 5 and 6, described in greater detail hereinafter.

As also demonstrated throughout FIGS. 1-4, the length of the support shaft 20 is such that a significant portion thereof 30 and 32 extends beyond the head 14 and the open end 28' of the channel 28 through which it passes. Accordingly, the support shaft 20 is dimensioned and structured to have movably mounted thereon at least one but in certain preferred applications a plurality of fixation rod clamps 30 and 32. Further, each of the clamps are initially rotatable about the support shaft 20 and are also movable therewith as the support shaft moves relative to and with the base 12. Therefore, each of one or more rod clamps 30 and 32 may be selectively disposed and oriented to clamp, grip or otherwise securely but removably engage a different fixation rod, such as of the type represented as 106 in the prior art representation of FIG. 9.

As is further noted, each of the one or more fixation rod clamps 30 and 32 comprises separated segments 30' and 32', which are initially separated from one another to facilitate clamping or gripping engagement with different ones of the fixation rods 106 with which they are used. However, the assembly 10 further comprises an adjustment assembly generally indicated as 36. The adjustment assembly 36 includes an adjustment nut or like structure 38 secured to a rotational knob or like member 40 both of which are preferably threaded (not shown) onto an outer or distal end of the support shaft 20. Accordingly, rotation of the adjustment nut 38 in an appropriate direction will cause an inward movement of the nut 38. This in effect will tighten and/or close the rod clamps 30 and 32, bringing them into immediately adjacent relation to one another. Concurrently, each of the rod clamps 30 and 32 will have their respective segments 30',30' and 32',32' close into a gripping or clamping engagement about different, corresponding fixation rods, which would be disposed within the open receiving portions 39 of each of the rod clamps 30 and 32.

Therefore, due to the relative movements of the base 12 relative to the coupling member 110; the support shaft 20 movable relative to the base 12 and the one or more rod clamps 30 and 32 on and relative to the support shaft 20, the one or more rod clamps 30 and 32 can be substantially universally positioned and/or oriented relative to the coupling member 10 and more specifically the pin clamp 104 to which it is connected.

Figure 6:
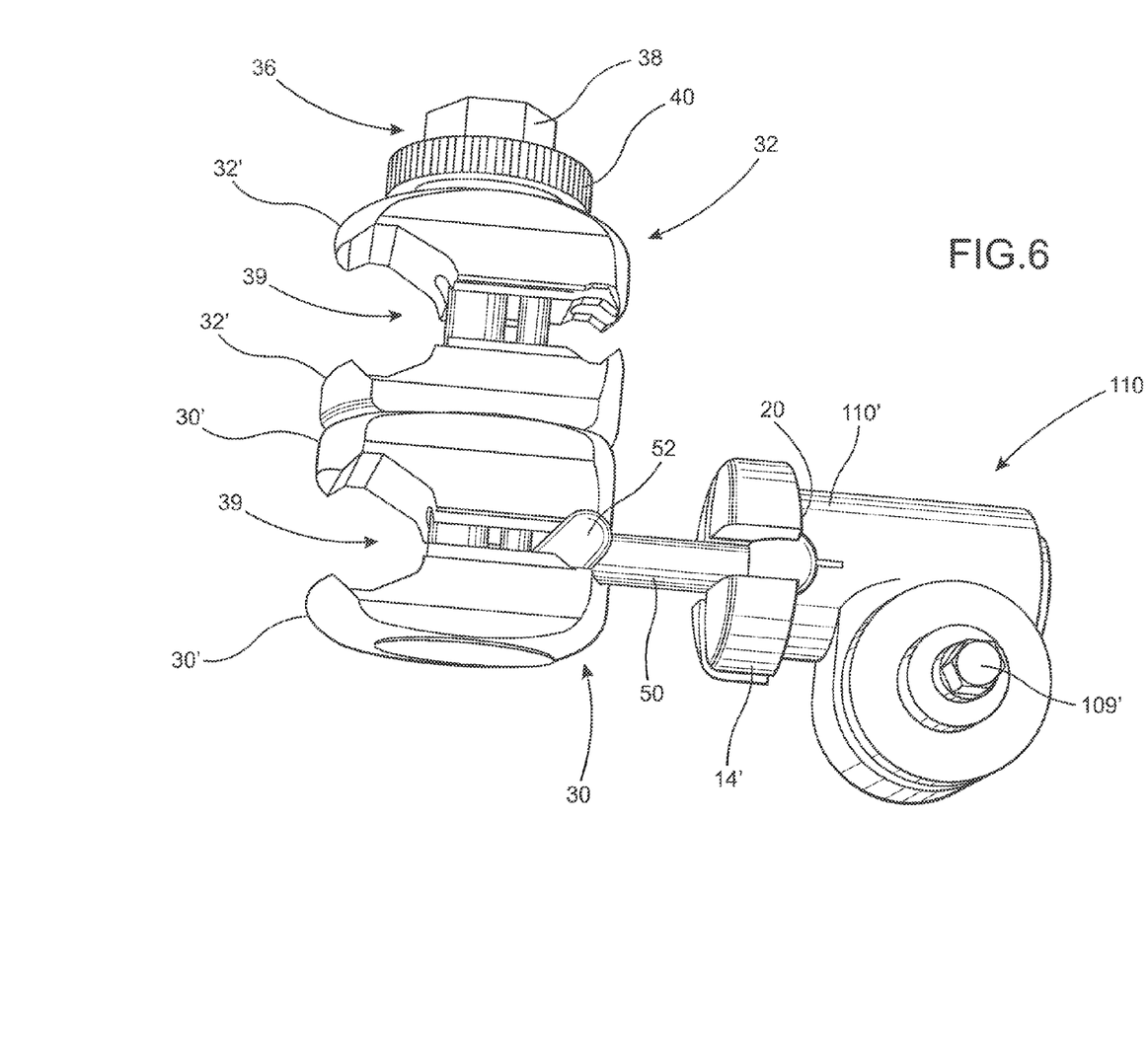
FIG. 6 is a side perspective view of the embodiment of FIG. 5.

As set forth above, an additional embodiment of the assembly is represented in FIGS. 6 and 7 and is generally represented as 10'. This embodiment may be considered at least partially structurally equivalent to the assembly 10 of the embodiment of FIGS. 1-4. As such, like parts include like numerical designations in the preferred embodiments of FIGS. 1-4 and FIGS. 6 and 7. However, in the embodiment of FIGS. 6 and 7, the assembly 10' includes a connecting link 50 having the ball and socket connection 22 movably connecting one end of the link 50 to the coupling member 110. The oppositely disposed outer or distal end of the link 50 has a substantially T-shaped configuration including a transverse segment 52. The segment 52 is disposed dimensioned and configured to be removably gripped or clamped within a receiving portion 39' of one of the rod clamps 30, 32 in order to interconnect the support shaft 20 in an operative position relative to the coupling member 110.

As also set forth above, structural modifications of the base 14, 14' are represented in FIG. 7. More specifically, the head portion 14' of the base 12' used in the embodiment of FIGS. 6 and 7 includes a plurality of channels 28 and 29 disposed in a "crossed" or perpendicular, transverse relation to one another. In contrast, the head 14 of the base 12 may only include a single channel 28. However, the versatility of the different embodiments 10 and 10' of the assembly is such that the base 12 and 12', as represented in FIGS. 1-7, could be used interchangeably if desired. As should be apparent, the provision of a plurality of two channels 28 and 29 in the head 14' provides an increased range of motion in that the link 50 may extend through at least a portion of either the channels 28 and 29 and extend out of corresponding opposite open ends thereof.

An additional orientation of the link 50 is disclosed as extending substantially linearly and/or coaxially outward relative to the length of the base 12' and or associated shank 16, 16'. However, it is further emphasized that the link 50 may also be positioned both rotationally and pivotally relative to the head 14' based on the provision of the ball and socket connection 22 as described in greater detail above.

Figure 8:
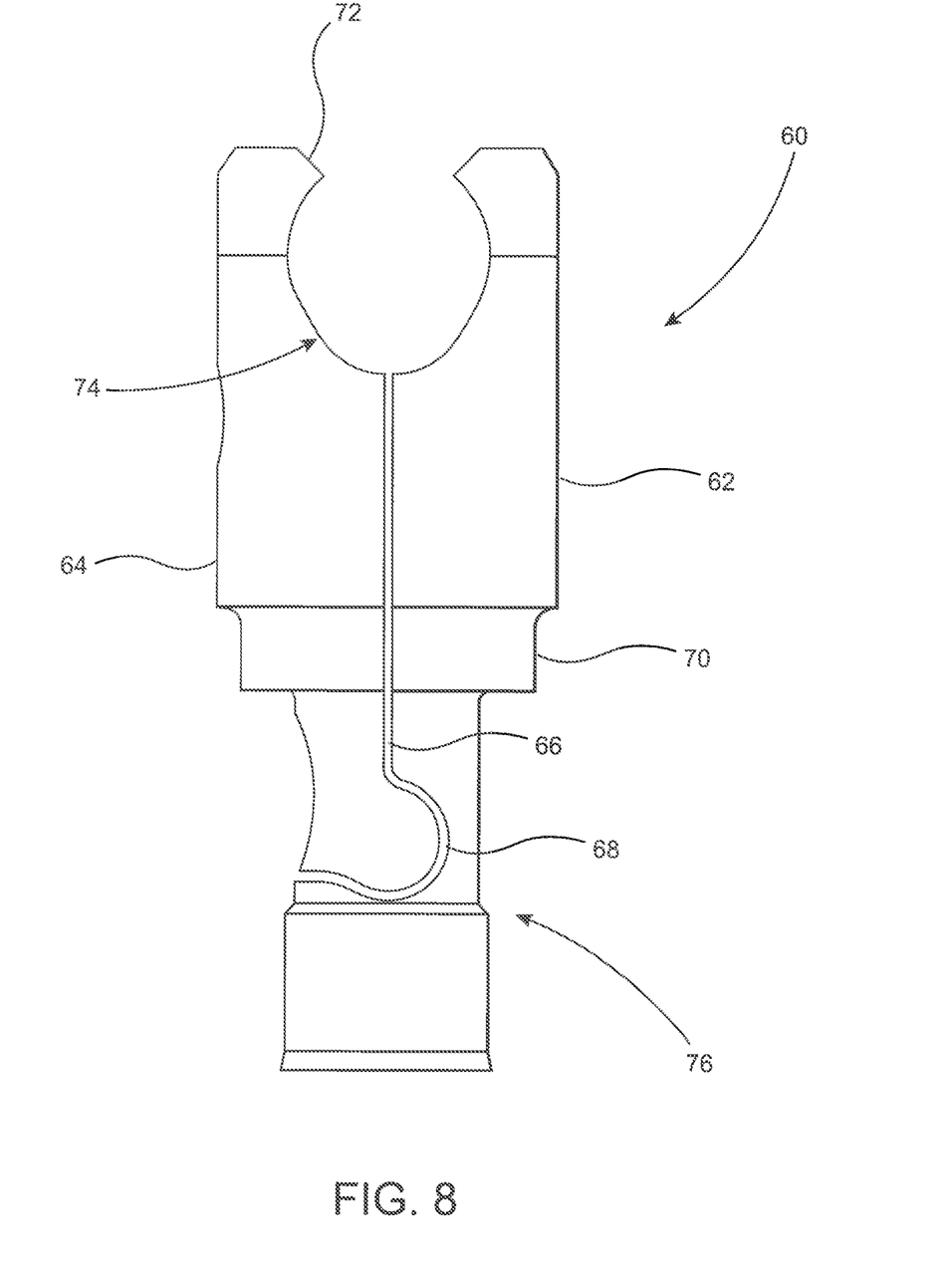
FIG. 8 is one embodiment of a rod clamp structurally modified to include to cooperative pieces.

FIG. 8 is directed to an additionally modified fixation rod clamp having a two-piece construction being generally indicated as 60. The clamp 60 includes segments 62 and 64 separated substantially longitudinally by a junction 66. Also, when connected together in an operative manner, as represented, a tongue and groove type connection generally indicated as 68 serves to facilitate attachment of the two segments 62 and 64. The tongue and groove connection 68 also facilitates alignment of corresponding and/or cooperative portions or components of the two segments 62 and 64. In order to maintain the two segments 62 and 64 in their assembled orientation, as represented in FIG. 8, a washer made of Silicon or other appropriate material, having at least some flexibility, may be disposed in surrounding relation to a receiving flange 70. As a result, minimal separation between the segments 62 and 64 may occur, such as when a bone fixation rod is forced through an open end, generally indicated as 72 into the rod receiving/gripping area 74. As should also be apparent the two-piece fixation rod clamp has a reduced transverse dimension at its lower portion generally indicated as 76. This facilitates a telescopic insertion thereof into a known, conventional and/or customized coupling member such as, but not limited to, coupling member 110 described above and shown throughout the accompanying Figures.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. An assembly for use in an external fixator, structured to adjustably interconnect at least one fixation rod to a pin clamp, said assembly comprising:
   a base movably connected to a pin clamp coupling member,
   a support shaft movably connected to said base and extending outwardly there from,
   at least one rod clamp movable with an adjustably connected to said support shaft,
   said movable connections of said base, said support shaft and said at least one rod clamp, relative to one another, defining a substantially universal disposition of said one rod clamp relative to the pin clamp.

2. The assembly as recited in claim 1 wherein said support shaft is positionable outwardly from and pivotal relative to said base through an arcuate path.

3. The assembly as recited in claim 2 wherein said support shaft is positionable radially outward from said base in substantially perpendicular relation to a length of said base.

4. The assembly as recited in claim 1 wherein said base and said support shaft are concurrently rotational relative to the coupling member.

5. The assembly as recited in claim 4 wherein said support shaft is rotational relative to said base.

6. The assembly as recited in claim 5 wherein said at least one rod clamp is movable with and relative to said support shaft.

7. The assembly as recited in claim 5 wherein said at least one rod clamp is rotationally connected to said support shaft.

8. The assembly as recited in claim 1 further comprising a plurality of rod clamps each movable with and movably connected to said support shaft; each of said plurality of rod clamps structurally adapted to be connected in stabilizing relation to a different one of a plurality of fixation rods.

9. The assembly as recited in claim 8 wherein said support shaft is movable with and relative to said base.

10. The assembly as recited in claim 9 wherein said base is movably positionable relative to the coupling member and the pin clamp.

11. An assembly as recited in claim 1 wherein said base includes an elongated configuration structurally adapted to be at least partially and rotationally inserted within said coupling member.

12. An assembly for use in an external fixator, structured to adjustably interconnect at least one fixation rod to a pin clamp, said assembly comprising:
- a base structurally adapted for movable, adjustable interconnection between the pin clamp and the at least one rod clamp,
- an elongate support shaft movable with said base and movably connected thereto,
- a plurality of rod clamps each structurally adapted to secure a different fixation rod to said support shaft,
- said plurality of rod clamps movably connected and adjustably positioned on said support shaft in adjacent relation to one another, and
- said base, said support shaft and said plurality of rod clamps movably interconnected relative to one another to define a substantially universal disposition of said plurality of rod clamps relative to the pin clamp.

13. The assembly as recited in claim 12 wherein said support shaft is pivotally connected to said base and movable relative thereto in an outwardly extended orientation, through an arcuate path.

14. The assembly as recited in claim 13 wherein said base comprises a head portion including at least one channel formed therein, said support shaft pivotal relative to said head portion, through said channel and along said arcuate path.

15. The assembly as recited in claim 14 wherein said arcuate path comprises a substantially 180° arc.

16. The assembly as recited in claim 14 wherein said support shaft is positionable radially outward from said base in substantially perpendicular relation to a length of said base, concurrent to disposition of said support shaft within said channel.

17. The assembly as recited in claim 14 further comprising an access opening formed on said base in communicating relation with said channel; said access opening disposed and dimensioned to facilitate passage of said support shaft there through into and out of movable connection with said base.

18. The assembly as recited in claim 17 wherein said base further comprises a shank portion connected to said head portion and structurally adapted to removably interconnect said base to the pin clamp; said access opening formed at least partially in said shank and disposed in communicating relation with said channel.

19. The assembly as recited in claim 14 wherein said channel comprises oppositely disposed open ends, said support shaft extending radially outward from said head portion, in substantially perpendicular relation to a length of said base, concurrent to disposition within said channel, through one of said open ends.

20. The assembly as recited in claim 14 wherein said channel comprises oppositely disposed open ends, said support shaft extending radially outward from said head portion, in substantially perpendicular relation to a length of said base, concurrent to extending within said channel, through either of said oppositely disposed open ends.

21. The assembly as recited in claim 12 further comprising a ball and socket connecting structure formed on and movably connecting said support shaft and said base.

22. The assembly as recited in claim 12 further comprising an adjustment assembly movably connected to the support shaft in adjusting relation to the plurality of rod clamps disposed thereon.

* * * * *